United States Patent [19]

Lickei et al.

[11] Patent Number: 4,959,156

[45] Date of Patent: Sep. 25, 1990

[54] BLOCK CO-POLYMERS USEFUL AS AQUEOUS DISPERSANTS

[75] Inventors: Donald L. Lickei, Wallingford, Conn.; Michael L. Rosin, Dellwood, Minn.; Ming Shen, Guilford, Conn.

[73] Assignee: Olin Corporation, Cheshire, Conn.

[21] Appl. No.: 335,656

[22] Filed: Apr. 10, 1989

Related U.S. Application Data

[62] Division of Ser. No. 79,554, Jul. 30, 1987, Pat. No. 4,847,410.

[51] Int. Cl.$^5$ ............................ C02F 5/12; C02F 1/00
[52] U.S. Cl. ............................ 210/701; 526/318.41; 560/180; 562/583
[58] Field of Search ............... 562/583; 560/180; 526/318.41; 210/701

[56] References Cited

U.S. PATENT DOCUMENTS

| | | | |
|---|---|---|---|
| 3,954,858 | 5/1976 | Lamberti et al. | 252/132 |
| 4,059,616 | 11/1977 | Lewis et al. | 526/66 |
| 4,338,239 | 7/1982 | Dammann | 524/549 |
| 4,469,615 | 9/1984 | Tsuruoka et al. | 210/701 |
| 4,471,100 | 9/1984 | Tsubakimoto et al. | 525/367 |
| 4,500,693 | 2/1985 | Takehara et al. | 526/240 |

FOREIGN PATENT DOCUMENTS 56-081320  7/1981  Japan.

Primary Examiner—Joseph L. Schofer
Assistant Examiner—Thomas McDonald, Jr.
Attorney, Agent, or Firm—Dale Lynn Carlson

[57] ABSTRACT

A process for preparing water-scale inhibitors and, more specifically, a neat process for preparing acrylic acid/ethylene glycol graft co-polymers and a method for their use as scale inhibitors.

8 Claims, No Drawings

BLOCK CO-POLYMERS USEFUL AS AQUEOUS DISPERSANTS

This application is a division, of application Ser. No. 07/079,554, filed Jul. 30, 1987, now U.S. Pat. No. 4,847,410.

Field of the Invention

This invention relates generally to water-scale inhibitors and, more specifically, to a solvent-free process for preparing acrylic acid/ethylene glycol graft co-polymers and a method for their use as scale inhibitors.

Background of the Invention

Water-scale formation in aqueous heat-exchange media is a formidable problem having adverse economic consequences since water-scale formed on the heat exchanger's walls impedes the heat exchange process. In an attempt to obviate this problem, various compounds have been suggested in the prior art as additives to aqueous heat exchange systems for the purpose of reducing the formation of water scale on the heat-exchange surfaces of these systems.

By way of illustration, U.S. Pat. No. 4,500,693 discloses a water-soluble co-polymer useful as a scale inhibitor and pigment dispersant. The co-polymer of this '693 patent comprises the product of the reaction of at least one (meth)acrylic acid-based monomer with a select allyl ether-based monomer. This reaction is identified in the paragraph bridging columns 4 and 5 of the '693 patent as being typically conducted in an aqueous, organic or mixed aqueous/organic solvent medium.

As another illustration, Japanese Kokai 56/081320, published on Jul. 3, 1981, discloses the reaction of polyethylene glycol-monoallyl ether with (meth)acrylic acid or a salt thereof to form a co-polymer said to be useful as a pigment dispersant and scale inhibitor. This Kokai discloses that the co-polymer is generally formed in an aqueous or organic solvent medium. In addition, Method 10 of the Kokai discloses a solvent-free reaction to produce a solid co-polymer. However, such a solid co-polymer is difficult to handle and thus impractical from a commercial processing standpoint.

In view of the large number of aqueous heat exchange systems employed in the chemical industry today, the development of new processes for making scale inhibitors is highly desired.

Summary of the Invention

In one aspect, the present invention relates to a process or preparing a liquid acrylic acid/acetate-capped polyethylene glycol-monollyl ether co-copolymer which comprises the steps of:
(a) reacting an acetylating agent with an allyl ether of polyethylene glycol to produce an acetate-capped polyethylene glycol-monoally ether, and
(b) reacting said acetate-capped polyethylene glycol-monoallyl ether with an acrylic compound selected from the group consisting of acrylic acid, methacrylic acid, and mixtures thereof, in a solvent-free reaction to produce said liquid acrylic acid/acetate-capped polyethylene glycol-monoallyl ether co-polymer.

In another aspect, the present invention relates to a method of inhibiting water-scale formation in an aqueous composition comprising adding to said aqueous composition an acrylic acid/acetate-capped polyethylene glycol-monoallyl ether co-polymer made in accordance with the above-described process.

Detailed Description of the Invention

In accordance with the present invention, a solvent-free process for producing liquid acrylic acid/acetate-capped polyethylene glycol-monoallyl ether co-polymers has now been discovered. The co-polymers thus prepared are excellent inhibitors for minimizing water scale formation in aqueous systems as measured by clay dispersion and calcium phosphate precipitation inhibition tests.

The co-copolymer preparation process of the present invention employs two steps. In accordance with the first step, and acetylating agent is reacted with an allyl ether of polyethylene glycol to produce an acetate-capped polyethylene glycol-monoallyl ether. Illustrative examples of useful acetylating agents includes acetic acid, acetic anhydride, acetyl chloride, and the like. The acetylating agent is preferably employed in an amount of between about 1.0 and about 1.8 (more preferably between about 1.0 and about 1.2) molar equivalents per molar equivalent of the allyl ether of polyethylene glycol reacted.

This first step reaction is preferably conducted at a temperature of between about 20° C. and about 180° C., more preferably between about 100° C. and about 165° C. and a pressure of between atmospheric and 10 atmospheres pressure, preferably at atmospheric pressure. This reaction is relatively rapid, preferably taking no more than a couple of hours to complete.

The first step reaction of the process of the present invention has been found by the present inventors to be necessary in order to enable production of a liquid co-polymer in the second step while permitting the use of desirably high amounts of acrylic compound as a reactant in the second step.

In the second step reaction, the acetatecapped polyethylene glycol-monoallyl ether is reacted with an acrylic compound (e.g., acrylic acid, methacrylic acid, or salts thereof) to produce the desired liquid co-polymer.

Thus, in this second step reaction the desired co-polymer is provided by reacting at least one (meth)acrylic acid-based monomer represented by the general formula (I):

wherein R is a hydrogen atom or methyl group and X is a hydrogen atom, alkali metal atom, alkaline earth metal atom, ammonium group, organic amine group, or alkyl group, with the acetate-capped polyethylene glycol-monoallyl ether produced in the first step reaction.

The co-polymer produced by this second step reaction contains repeating units represented by the empirical formulas (II) and (III) as follows:

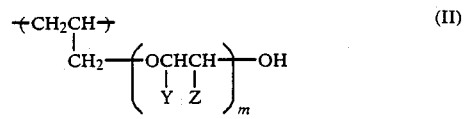

wherein Y and Z are individually selected from the group consisting of hydrogen and

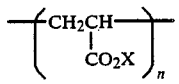

wherein m and n are integers, and

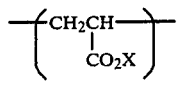

wherein X is defined above.

This second step reaction is preferably conducted at atmospheric pressure, although superatmospheric pressures of up to 10 atmospheres or higher may be used if desired. This second step reaction is preferably conducted at an elevated reaction temperature of between 50° C. and 200°, more preferably between 75 C. and 175° C. Typical reaction times are between a few minutes and several hours, preferably between 10 minutes and three hours. The reaction is suitably effected in the presence of a free-radical initiator.

Useful free-radical initiators include the azo compounds such as azobisisobutylnitrile (AIBN) or organic peroxides such as benzoyl peroxide, cumene hydroperoxide, di-tert-butylperoxide, and the like. Additionally, an accelerator such as the well-known amine compounds may be employed.

The free radical initiator is suitably used in an amount of between about 0.05 and about 20 weight percent, preferably between about 0.1 and about 5 weight percent, based on the total weight of the second step reaction mixture.

In an alternate and non-preferred embodiment of the present invention, uncapped polyethylene glycol-monoallyl ether can be used as a co-reactant with the acetate-capped polyethylene glycol-monoallyl ether. If the acetate-capped material is used alone, it is suitably employed in an amount of between about 40 and about 90 (more preferably between about 50 and about 80, most preferably between about 50 and about 70) weight percent based upon the total weight of acetate-capped material plus acrylic compound employed. Conversely, the acrylic compound is suitably employed in an amount of between about 10 and about 60 (more preferably between about 20 and about 50, most preferably between about 30 and about 50) weight percent based upon the total weight of acetate-capped material plus acrylic compound employed. If the uncapped compound is also used, generally amounts of no less than 50 weight percent of capped ether plus uncapped ether is employed based on the total weight of capped ether plus uncapped ether plus acrylic compound used.

The co-polymers prepared in the process of the present invention are useful in inhibiting water scale formation in agueous systems, particularly aqueous heat exchange systems such as industrial cooling towers.

The following examples are intended to illustrate, but in no way limit the scope of, the present invention.

EXAMPLE 1

Two-Step Process for Preparing Co-Polymers

Step (a)

To a 5-liter 3-neck round-bottom flask equipped with a water-cooling condenser, a thermometer, and a mechanical stirrer was charged 3.0 kg (7.5 mol) of polyethylene glycol-monoallyl ether (molecular weight 400) and 1.3 kg (13 mol) of acetic anhydride. The reaction mixture was stirred and heated to 160° C. under a nitrogen atmosphere. After heating at 160° C. for one hour, the reaction mixture was cooled to 120° C. and stripped at 1 mm Hg for five hours while holding the pot temperature at 120° C. 3.3 kg of the acetylated polyethylene glycol-monoallyl ether were thus obtained from the reaction flask and 0.94 kg of the volatile components (excess unreacted acetic anhydride and acetic acid as the reaction side product) were recovered from the vacuum trap.

Step (b)

To a 5-liter, 4-neck round-bottom flask equipped with two water cooling condensers, one mechanical stirrer, and one thermometer was charged 1.2 kg (2.72 mol) of the acetylated polyethylene glycol-monoallyl ether prepared in step (a). After heating to 150° C. under a nitrogen atmosphere, two feed streams of 10 g (0.068 mol) of di-tert-butylperoxide and 800 g (11.1 mol) of acrylic acid were introduced from the two cooling condensers through two glass tubings while maintaining the reaction temperature at 150° C. The additions were completed, respectively, in 27 and 45 minutes for the former and latter. After post-reacting at 150° C. for 10 minutes, 1550 g of distilled water were slowly added in. A light yellow 56 percent active polymer solution was obtained after cooling to ambient temperature. The viscosity of the polymer solution was determined by a Brookfield viscometer model RVT as 649 cps at 23° C. The polymer performance tests are summarized in TABLES I and II below.

EXAMPLE 2

The same procedure of EXAMPLE 1 (b) was followed except that 1240 g (2.81 mol) of the acetylated polyethylene glycol-monoallyl ether.760 g (1.06 mol) of acrylic acid, and 5.0 g (0.034 mol) of di-tert-butylperoxide were used. The additions of di-tert-butylperoxide and acrylic acid were completed in 30 and 43 minutes, respectively. The reaction temperature was maintained at 140° C., and the reaction mixture was post-reacted at 140° C. for 15 minutes. A light yellow polymer solution was obtained. The viscosity of the polymer solution was determined as 299 cps at 23° C. The results of the polymer performance tests are summarized in TABLES I and II below.

EXAMPLE 3

The same procedure of EXAMPLE 1 (b) was followed except that 1160 g (2.62 mol) of the acetylated polyethylene glycol-monoallyl ether, 840 g (11.7 mol) of acrylic acid, and 15 g (0.10 mol) of di-tert-butylperoxide were used. The additions of di-tert-butylperoxide and acrylic acid were completed in 30 and 43 minutes, respectively. The reaction temperature was maintained at 140° C., and the reaction mixture was post-reacted at 140° C. for five minutes. A light yellow polymer solution was obtained. The viscosity of the polymer solution was determined as 489 cps at 23° C. The results of the polymer performance tests are summarized in TABLES I and II below.

EXAMPLE 4

The same procedure of EXAMPLE 1 (b) was followed except that 1240 g (2.81 mol) of the acetylated polyethylene glycol-monoallyl ether, 760 g (1.06 mol) of acrylic acid, and 15 g (0.10 mol) of di-tert-butylperoxide were used. The additions of di-tert-butylperoxide and acrylic acid were completed in 15 and 43 minutes, respectively. The reaction temperature was maintained at 160° C., and the reaction mixture was post-reacted at 160° C. for five minutes. A light yellow polymer solution was obtained. The viscosity was determined as 429 cps at 23° C. The results of the polymer performance tests are summarized in TABLES I and II below.

EXAMPLE 5

To a 1-liter, 4-neck round-bottom flask equipped with one water cooling condenser, one mechanical stirrer and one thermometer was charged 186 g (0.42 mol) of the acetylated polyethylene glycol-monoallyl ether. After heating to 130° C. under a nitrogen atmosphere, 1.5 g (0.010 mol) of di-tert-butylperoxide were added in one fraction before the addition of 114 g (1.58 mol) of acrylic acid was started. The addition of acrylic acid was completed in 2 ½ hours while maintaining the reaction temperature 130°C. After post-reacting for 15 minutes, 398 g distilled water were slowly added. The polymer solution was cooled to ambient temperature to give a light yellow color. The viscosity of this 43 percent active polymer solution was determined by a Brookfield viscometer model RVT as 157 cps at 23° C. The results of the polymer performance tests are summarized in TABLES I and II below.

EXAMPLE 6

The procedure of EXAMPLE 5 was followed except that 174 g (0.39 mol) of the acetylated polyethylene glycol-monoallyl ether, and 126 g (1.75 mol) of acrylic acid were used. The reaction temperature was maintained at 150° C., and the reaction mixture was post-reacted for five minutes. A light yellow, 43 percent active polymer solution was obtained. The viscosity of the polymer solution was determined as 120 cps at 23° C. The results of the polymer performance tests are summarized in TABLES I and II below.

EXAMPLE 7

The procedure of EXAMPLE 5 was followed except that 180 g (0.41 mol) of the acetylated polyethylene glycol-monoallyl ether, 120 g (1.67 mol) of acrylic acid, and 4.5 g (0.031 mol) of di-tert-butylperoxide were used. The addition of acrylic acid was completed in three hours, and the reaction mixture was post-reacted for 10 minutes. A light yellow, 43 percent active polymer solution was obtained. The viscosity of the polymer solution was determined as 130 cps at 23° C. The results of the polymer performance tests are summarized in TABLES I and II below.

EXAMPLE 8

The procedure of EXAMPLE 5 was followed except that 195 g (0.44 mol) of the acetylated polyethylene glycol-monoallyl ether, 105 g (1.46 mol) of acrylic acid, 2 g (0.014 ml) of di-tert-butylperoxide, and 236 g distilled water were used. The addition of acrylic acid was completed in 2.6 hours while maintaining the reaction temperature at 140° C. The reaction mixture was post-reacted at 140° C. for 10 minutes. A light yellow polymer solution of 56 percent active polymer was obtained. The viscosity of the polymer solution was determined as 584 cps at 23° C. The results of the polymer performance tests are summarized in TABLES I and II below.

EXAMPLE 9

The same experimental assembly used in EXAMPLE 5 was adopted, except that a 5-liter, 4-neck round-bottom flask was used. To the reactor was added 1.2 kg (2.70 mol) of the acetylated polyethylene glycol-monoallyl ether. After heating to 150° C., 2.5 g (0.017 mol) of di-tert-butylperoxide and 800 g (11.1 mol) of acrylic acid were sequentially added while maintaining the reaction temperature at 150° C. Another 2.5 g (0.017 mol) of di-tert-butylperoxide were added after the addition of acrylic acid was halfway completed. The total addition of acrylic acid was completed in 43 minutes. The reaction mixture was post-reacted at 150° C. for 10 minutes, and then 1550 g of distilled water were added. After cooling to room temperature, a light yellow polymer solution of 66 percent active polymer was obtained. The results of the polymer performance tests are summarized in TABLES I and II below. A small quantity of the polymer solution was stripped of water under reduced pressure (0.1 mm Hg). The residue was covered with $CH_2Cl_2$ and methylated with diazomethane generated from N-methyl-N'-nitro-N-nitrosoguanidine according to the procedure in Fieser & Fieser's "Reagents for Organic Synthesis", Vol. 1, p. 192. The methyl ester was then subjected to GPC analysis which disclosed a molecular weight of 9,945 and dispersity of 44.5

Comparative Example A

To a 500 ml, 4-neck round-bottom flask, equipped with two water cooling condensors, one mechanical stirrer and one thermometer was charged 120 g (0.27 mol) of the acetylated polyethylene glycol-monoallyl ether and 80 g of 4-methyl-2-pentanone. The reaction mixture was heated to 105° C. under a nitrogen atmosphere, then charged in dropwise 80 g (1.1 mol) of acrylic acid and a solution of 1.4 g (3.2 mmol) of 1,1-bis(t-butyl peroxy) cyclohexane (75 percent solution, USP-400P from Witco Chemical Corporation) in 80 g of 4-methyl-2-pentanone in two separate streams from the two cooling condensors. The additions were completed in two hours while maintaining the reaction temperature at 105° C. After post-reacting at 105° C. for additional two hours, the reaction mixture was cooled to ambient temperature. A polymer mass separated out from 4-methyl-2-pentanone solvent was obtained. A small sample of the polymer mass was pump dried and then used for the polymer performance tests. The results are summarized in TABLES I and II below.

Comparative Example B

The same procedure of Comparative Example A was followed except that water was used as the solvent instead of 4-methyl-2-pentanone, sodium persulfate (2 g) was used as the radical catalyst instead of USP-400P and the reaction temperature for addition and post-reaction was set at 95° C. instead of 105° C. A clear aqueous polymer solution was thus prepared. The results of the polymer performance tests are summarized in TABLES I and II below.

Comparative Example C

The same procedure of Comparative Example A was followed except that isopropanol was used as the solvent instead of 4-methyl-2-pentanone, benzoyl peroxide (2 g) was used as the radical catalyst instead of USP- 400P, and the reaction temperature for addition and post-reaction was set at 82° C. instead of 105° C. A clear polymer solution in isopropanol was thus prepared. The results of polymer performance tests are summarized in TABLES I and II below.

Comparative Example D

The same procedure of Comparative Example A was followed except polyethylene glycol-monoallyl ether (molecular weight 400) was used instead of the acetylated polyethylene glycol-monoallyl ether. A polymer mass separated out from 4-methyl-2-pentanone solvent was thus obtained. A small dry sample of the polymer mass was used for the polymer performance tests The results are summarized in TABLES I and II below.

Comparative Example E

The same procedure of Comparative Example B was followed except that polyethylene glycol-monoallyl ether (molecular weight 400) was used instead of the acetylated polyethylene glycol-monoallyl ether. A clean aqueous polymer solution was thus obtained. The results of polymer performance tests are summarized in TABLES I and II below.

Comparative Example F

The same procedure of Comparative Example C was followed except that polyethylene glycol-monoallyl ether (molecular weight 400) was used instead of the acetylated polyethylene glycol-monoallyl ether. A clean polymer solution in isopropanol was thus obtained. The results of polymer performance tests are summarized in TABLES I and II below.

Comparative Example G

To a 500 ml, 4-neck round-bottom flask equipped with one water cooling condenser and one mechanical stirrer was added 22 g (0.040 mol) of polyethylene glycol-monoallyl ether (molecular weight 550). After heating to 155° C. under a nitrogen atmosphere, a mixture prepared by dissolving 1.8 g (0.0094 mol) of 2,2'-azobis (2-methylbutanenitrile) in 50 g (0.091 mol) of polyethylene glycol-monoallyl ether (molecular weight 550) was added simultaneously with another aqueous acrylic acid solution prepared from 72 g (1.0 mol) of acrylic acid in 144 g of distilled water. The reaction temperature dropped rapidly below 100° C. after the addition of aqueous acrylic acid was started. The first and the second additions were completed in 3 and 3¼ hours, respectively, while the reaction temperature was maintained at 92° C. The mixture was post-reacted at 92° C. for another 1½ hours at the end of additions, and then poured out. After cooling to ambient temperature, a clear viscous product was obtained. The results of the polymer performance tests are summarized in TABLES I and II below.

Comparative Example H

The same procedure of Comparative Example G was followed except that two different feed streams were prepared. One was prepared from 1.3 g (0.0014 mol) of mercaptoacetic acid and 2.0 g (0.0088 mol) of ammonium persulfate in 80 g of distilled water, and another was prepared from 50 g (0.091 mol) of polyethylene glycol-monoallyl ether (molecular weight 550) and 108 g (1.5 mol) of acrylic acid in 100 g of distilled water. A clear polymer solution was obtained. The results of the polymer performance tests are summarized in TABLES I and II below.

Comparative Example I

To a 500 ml, 4-neck round-bottom flask equipped with one water cooling condenser and one mechanical stirrer was added 75 g (0.14 mol) of polyethylene glycol-monoallyl ether (molecular weight 550), 30 g of distilled water, 1.15 g (0.013 mol) of mercaptoacetic acid, 15 g (0.21 mol) of acrylic acid, and an aqueous solution of 0.38 g (0.16 mmol) of a $Na_2S_2O_8$ in 10 g of distilled water. The resulting exotherm heated the reaction mixture to 50° C. which was then raised to 90° C. by external heating. After cooling to 30° C., another cycle of additions of 1.15 g (0.013 mol) of mercaptoacetic acid, 15 g (0.21 mol) of acrylic acid, and an aqueous solution of 0.3 g (1.4 mmol) of ammonium persulfate in 25 g of distilled water was followed and completed by exothermic/external heating to 90° C. Three more cycles of cooling, sequential addition, and heating were operated. The reaction mixture was post-reacted at 90° C. for two hours and then cooled to ambient temperature. A clean, viscous product was obtained. The polymer was stripped of most of the water under reduced pressure (0.1 mm Hg) and methylated with diazomethane generated from N-methyl-N'-nitro-N-nitrosoguanidine. The GPC analysis disclosed a polymer molecular weight centered around 5,000. The results of the polymer performance tests are summarized in TABLES I and II below.

TEST PROCEDURES AND TEST RESULTS

Clay Dispersion Capability Test

Calcium chloride stock solution (300 ml, 1000 $Ca^{++}$ as $CaCO_3$) and distilled water (1200 ml) were combined and mixed thoroughly. Approximately 400 ml of the solution were poured into a blender container. The solution was mixed on the lowest blender speed (3500 rpm) while 1.5 g of the clay (Englehard Ultrawhite 90) were added to the solution. The resulting mixture was then mixed at the highest speed (2100 rpm) for 10 minutes and was then added back to the remainder of the original solution which was stirring (mechanical stirrer set at about 200 rpm) in a 2-1 beaker. The mixture was agitated for 5 minutes, and the pH was adjusted to 8.5 by addition of 1 percent sodium hydroxide solution. The mixture was agitated for an additional 5 minutes after the pH adjustment with mixture occasionally removed from the bottom of the beaker (by means of a stopcock attached to the beaker) to prevent excessive settling of the clay. At the end of the agitation period, a number of 100 ml samples (as more clearly identified in TABLE I) were drained into 100 ml milk dilution bottles (each bottle was filled with approximately 50 ml of mixture before filling any bottles to the 100 ml mark). To all but one of the bottles was added 0.20 ml of a 0.5 percent active solution of a polymer while nothing was added to the last bottle (the control). The bottles were agitated for one minute by repeated inversion. After agitating, the bottles were allowed to remain undisturbed for 24 hours. An aliquot was then removed from each bottle by inserting a 5 ml graduated pipette to the 3 ml mark and drawing up a 3.0 ml sample. The percent transmission of each sample was determined as compared to a distilled water blank at 381 nm. For each sample a calculation of the degree of dispersion was made where: degree of dispersion = 1/10[%T (no treatment) - %T (polymer)].

TABLE I
Clay Dispersion Capability Test Results

| | Degree of Dispersion | |
|---|---|---|
| Example | Sample | Comparison Sample S-SMA 1000L* |
| 1 | 7.4 | 4.8 |
| 2 | 7.4 | 4.8 |
| 3 | 7.4 | 4.8 |
| 4 | 7.3 | 4.8 |
| 5 | 8.6 | 6.5 |
| 6 | 6.5 | 7.8 |
| 7 | 7.7 | 7.8 |
| 8 | 7.8 | 6.4 |
| 9 | 8.5 | 7.3 |
| Comparative Example A | 3.4 | 2.9 |
| Comparative Example B | 4.1 | 2.9 |
| Comparative Example C | 3.8 | 2.9 |
| Comparative Example D | 1.7 | 2.9 |
| Comparative Example E | 5.3 | 2.9 |
| Comparative Example F | 2.9 | 2.9 |
| Comparative Example G | 5.6 | 8.7 |
| Comparative Example H | 6.8 | 6.2 |
| Comparative Example I | 5.1 | 6.0 |
| Comparative Example J (using PAA**) | 0.4 | 2.5 |

*S-SMA 1000L is a commercial co-polymer of sulfonated styrene-maleic acid available from Chemlink Petroleum.
**PAA is a commercial polyacrylic acid available from Celanese Corporation.

The results presented in TABLE I above demonstrate that the co-polymers of EXAMPLES 1 through 9 provided improved results in terms of clay dispersion capability as compared to the PAA (Comparative Example J) sample and provided comparable or improved results relative to the aqueous or organic solvent preparations (Comparative Examples A through J) as well as comparison compositions prepared using the excellent commercial water scale inhibitor S-SMA 1000L.

TEST PROCEDURES AND TEST RESULTS

Calcium Phosphate Precipitation Inhibition Test

Two stock solutions were prepared as follows: solution A by mixing 600 ml of calcium stock solution (1000 ppm of $Ca^{++}$ as $CaCO_3$) and 600 ml of distilled water, and solution B by mixing 24 ml of phosphate stock solution (800 ppm as orthophosphate) and 1176 ml of distilled water. Both stock solutions were then adjusted to pH 9 with 1 percent sodium hydroxide. To each of a series of bottles was then added a 50 ml portion of solution A. To all but one of the bottles (the control) was then added 0.2 ml of 0.5 percent active solution of a polymer (the control bottle had no polymer). To each of the bottles was then added 50 ml of solution B while stirring. The bottles were then placed in an oven held at 70° C.

The bottles were removed from the oven after 18 hours and filtered while hot through a 0.45 micron filter (Gelman GN-6 membrane filter). The phosphate level in each sample was determined after cooling using the Hach reactive amino acid method. A 5 ml aliquot from a sample was placed in a test tube to which 0.2 ml of Hach Molybdate Reagent was then added. This was followed by the addition of 0.2 ml of Hach Amino Acid Reagent. The test tube was then shaken and allowed to stand for 12 minutes. The percent transmission of 880 nm was measured as compared to a distilled water blank. The ppm of phosphate was then calculated using the following calibration curve: ppm phosphate = (1/995-log%T)/0.0307.

TABLE II
Calcium Phosphate Precipitation Inhibition Test Results

| | PPM Phosphate | |
|---|---|---|
| Example | Sample | Comparison Sample S-SMA 1000L* |
| 1 | 5.48 | 7.42 |
| 2 | 5.48 | 7.42 |
| 3 | 5.81 | 7.42 |
| 4 | 5.16 | 7.42 |
| 5 | 6.45 | 8.39 |
| 6 | 5.81 | 8.39 |
| 7 | 6.77 | 8.39 |
| 8 | 5.81 | 8.39 |
| 9 | 4.84 | 8.39 |
| Comparative Example A | 1.29 | 9.03 |
| Comparative Example B | 5.16 | 9.03 |
| Comparative Example C | 6.13 | 9.03 |
| Comparative Example D | 0.97 | 9.03 |
| Comparative Example E | 5.48 | 9.03 |
| Comparative Example F | 6.13 | 9.03 |
| Comparative Example G | 2.93 | 8.06 |
| Comparative Example H | 4.52 | 8.06 |
| Comparative Example I | 3.23 | 8.06 |
| Comparative Example J (using PAA**) | 0.97 | 9.03 |

*S-SMA 1000L is a commercial co-polymer of sulfonated styrene-maleic acid available from Chemlink Petroleum.
**PAA is a commercial polyacrylic acid available from Celanese Corporation.

The results presented in TABLE II above demonstrate that the co-polymers of Examples 1 through 9 provided improved results in terms of calcium phosphate dispersion capability as compared to the PAA comparison (Comparative Example J) and provided comparable or improved results relative to the aqueous or organic solvent preparations (Comparative Examples A through J) provided slightly inferior results to those provided by the excellent commercial water-scale inhibitor S-SMA 1000L.

What is claimed is:

1. A method of inhibiting water-scale formation in an aqueous composition comprising adding to said aqueous composition a liquid acrylic acid/acetate-capped polyethylene glycol-monoallyl ether co-polymer prepared by a process which comprises the steps of:
   (a) reacting an acetylating agent with an allyl ether of polyethylene glycol to produce an acetate-capped polyethylene glycol-monoallyl ether, and
   (b) reacting said acetate-capped polyethylene glycol-monoallyl ether with an acrylic compound selected from the group consisting of acrylic acid, methacrylic acid, and mixtures thereof, in a solvent-free reaction to produce said liquid acrylic acid/acetate-capped polyethylene glycol-monoallyl ether co-polymer.

2. The method of claim 1 wherein the amount of said acetylating agent reacted in step (a) is between about 1.0 and about 1.8 molar equivalents per molar equivalent of said allyl alcohol of polyethlyene glycol reacted.

3. The method of claim 1 wherein the amount of said acetylating agent reacted in step (a) is between about 1.0 and about 1.2 molar equivalents per molar equivalent of said allyl alcohol of polyethlyene glycol reacted.

4. The method of claim 1 wherein the reaction of step (b) is effected in the presence of a free radical initiator.

5. The method of claim 1 wherein said free radical initiator is selected from the group consisting of azo compounds, peroxides, and mixtures thereof.

6. The method of claim 1 wherein the reaction of step (b) employs an amount of acrylic compound of between about 10 and about 60 weight percent based on the total weight of said acrylic compound plus said capped polyethylene glycol-monoallyl ether.

7. The process of claim 1 wherein the reaction of step (b) employs an amount of acrylic compound of between about 20 and about 50 weight percent based on the total weight of said acrylic compound plus said capped polyethylene glycol-monoallyl ether.

8. The process of claim 1 wherein the reaction of step (b) employs an amount of acrylic compound of between about 30 and about 50 weigh percent based on the total weight of said acrylic compound plus said capped polyethylene glycol-monoallyl ether.

* * * * *